(12) United States Patent
Schaefer et al.

(10) Patent No.: US 9,026,252 B2
(45) Date of Patent: May 5, 2015

(54) EXTRACTIVE DISTILLATION CONTROLS

(71) Applicants: Robert Alan Schaefer, Houston, TX (US); John J. Monson, League City, TX (US)

(72) Inventors: Robert Alan Schaefer, Houston, TX (US); John J. Monson, League City, TX (US)

(73) Assignee: ExxonMobil Chemical Patents Inc., Baytown, TX (US)

(*) Notice: Subject to any disclaimer, the term of this patent is extended or adjusted under 35 U.S.C. 154(b) by 92 days.

(21) Appl. No.: 13/683,588

(22) Filed: Nov. 21, 2012

(65) Prior Publication Data

US 2013/0173061 A1 Jul. 4, 2013

Related U.S. Application Data

(60) Provisional application No. 61/581,813, filed on Dec. 30, 2011.

(51) Int. Cl.
| | |
|---|---|
| *G05B 11/01* | (2006.01) |
| *C07C 7/10* | (2006.01) |
| *C07C 7/11* | (2006.01) |
| *C07C 7/08* | (2006.01) |

(52) U.S. Cl.
CPC . *G05B 11/01* (2013.01); *C07C 7/10* (2013.01); *C07C 7/11* (2013.01); *C07C 7/08* (2013.01)

(58) Field of Classification Search
CPC ............ G05B 11/01; C07C 7/10; C07C 7/11; C07C 7/08; C07C 15/02
USPC ............... 700/266, 17, 18, 83, 268, 269, 270, 700/271–273; 702/22, 31, 32
See application file for complete search history.

(56) References Cited

U.S. PATENT DOCUMENTS

| | | |
|---|---|---|
| 2,773,918 A | 12/1956 | Stephens |
| 3,361,664 A | 1/1968 | Broughton et al. |
| 7,288,184 B2 | 10/2007 | van Nuland et al. |
| 7,326,823 B2 | 2/2008 | Williams et al. |
| 7,739,217 B2 | 6/2010 | Kral et al. |
| 8,201,696 B2 | 6/2012 | Monson |
| 2012/0073951 A1 | 3/2012 | Noe et al. |

OTHER PUBLICATIONS

Barnicki et al., "Separation system synthesis: a knowledge-based approach. 1. Liquid mixture separations", Industrial & Engineering Chemistry Research, vol. 29. No. 3. Mar. 1, 1990, pp. 421-432.
Polke et al. "Integration of knowledge-based systems in process control Engineering", Ullmann's Encyclopedia of Industrial; Chemistry, Jun. 15, 2000, pp. 387-410.
Choi et al., International Application No. PCT/US2012/060330, filed Oct. 16, 2012.

*Primary Examiner* — Shogo Sasaki
(74) *Attorney, Agent, or Firm* — Amanda K. Jenkins

(57) ABSTRACT

The invention concerns an improvement in the monitoring and control systems used in a liquid-liquid extraction unit or an extractive distillation unit for the separation of aromatic hydrocarbons from non-aromatic hydrocarbons.

4 Claims, 2 Drawing Sheets

EXTRACTIVE DISTILLATION CONTROLS

PRIORITY CLAIM

This application claims the benefit of Provisional Application No. 61/581,813, filed Dec. 30, 2011, the disclosure of which is incorporated by reference in its entirety.

BACKGROUND OF THE INVENTION

1. Field of the Invention

The present invention relates to hydrocarbon separation, and more particularly to extraction, including liquid-liquid solvent extraction units and extractive distillation units.

2. Description of the Related Art

Aromatic hydrocarbons, such as benzene, toluene and xylenes (collectively, "BTX"), serve as important building blocks for a variety of plastics, foams and fibers. Often these compounds are produced via catalytic reformation of naphtha through steam cracking of naphtha or gas oils, or other methods where substantial amounts of non-aromatic compounds are present. When simple distillation or fractionation is not a cost effective or practical method for separation, liquid-liquid extraction or extractive distillation techniques are used. Such extraction techniques separate a desired substance selectively from a mixture or remove unwanted impurities from solution, and, in the context of the invention described hereinbelow, aromatic hydrocarbon separation from non-aromatic hydrocarbons. A solvent is typically used which exhibits a higher affinity for the aromatic compounds than the non-aromatic compounds, thereby selectively extracting the aromatic compounds from the mixture of aromatics and non-aromatics. The aromatic species of interest can then be isolated from the solvent by distillation, adsorptive separation techniques, and the like.

One widely used solvent extraction technique is the Sulfolane™ Process to recover high purity aromatics from hydrocarbon mixtures, which is discussed in numerous patents and other literature too numerous to cite. The process uses a combination of liquid-liquid extraction and extractive distillation in a single, integrated design, and employs tetrahydrothiophene-1,1-dioxide (or "sulfolane") as a solvent and water as a co-solvent. Other solvents conventionally used in liquid-liquid extraction include oxygen-containing species such as tetraethylene glycol and nitrogen-containing species such as N-methyl pyrolidine, each having similar issues that lead to decreasing the capacity of the extraction process, as well as their own unique problems.

FIG. 1 depicts a schematic view of an illustrative system 400 for separating high purity aromatics from a hydrocarbon mixture. Particularly desired products include benzene, toluene, xylene, and mixtures thereof (collectively, "BTX"), which are typically obtained in a desired purity ("on-spec") by further distillation or other methods downstream of the illustrative system 400. Conveniently this benzene and or toluene product fractionation section may be fully or partially heat integrated to provide feed preheating and or reboiling duty to the benzene and or toluene columns with other equipment in the installed facilities outside of System 400. Various embodiments are possible to make the heat integration feasible in order to create sufficient temperature differential between the heat supply source and the benzene and toluene columns that are receiving the heat. Examples include but are not limited to: raising the pressure in the column that is supplying the heat or lowering the pressure which might include operating under vacuum conditions in the benzene or toluene columns that are receiving the heat. In addition to one or more liquid-liquid extractor unit(s) 100 described above, the system 400 includes one or more extractive distillation units 410, water strippers 420, water wash columns 430, and recovery columns 440. In one or more embodiments, the system 400 can further include one or more heat exchangers (three are shown 445, 450, 455), one or more steam generators 460, and one or more water/hydrocarbon separators (two are shown 465, 470). Certain other devices, such as compressors, valves, column trays and packings, and the like, are not shown for convenience of view, however such devices would be apparent to one of ordinary skill in the art.

Within the extractor 100, a hydrocarbon mixture via line 145 (entering the extractor 100 at one or more locations) and a circulating solvent via line 150 can be contacted or otherwise mixed with one another in a countercurrent manner. The internal details of the various apparatus such as liquid-liquid extractor 100, extractive distillation unit 410, stripper 420, and column 440 do not form a part of the present invention per se except as explicitly pointed out herein below, but rather have been described in the prior art such as in U.S. Pat. No. 7,288,184, U.S. Patent Application Publication 2010-0096321, and more recently U.S. Provisional Application No. 61/566,116, filed Dec. 2, 2011, and may consist of various trays, gratings, packings, demister pads, and the like. Within the liquid-liquid extractor 100 the solvent extracts or otherwise separates at least a portion of the aromatic hydrocarbons from the multi-component hydrocarbon introduced via line 145 to provide a solvent enriched in aromatic hydrocarbons ("rich solvent") via line 155 and a raffinate having a reduced content of aromatic hydrocarbons via line 160. The solvent is advantageously Sulfolane™ but numerous other suitable materials for separating aromatic compounds from non-aromatic compounds are known in the art. The hydrocarbon feed via line 145 can be or include a mixture of aromatics and non-aromatics, typically in the C5-C10 range, and may also be or include a heavier refinery cut.

The rich solvent via line 155 is introduced to the heat exchanger 445 to transfer heat from the lean solvent introduced via line 462 to provide a heated rich solvent via line 447 and a cooled lean solvent via line 150. The heated rich solvent via line 447 can be introduced to the stripper 410 to provide a less-aromatic rich hydrocarbon via line 412 and a solvent further enriched in aromatic hydrocarbons via line 414.

The raffinate in line 160 can be introduced to the raffinate wash column 430 which can separate at least a portion of the solvent in the raffinate to provide a raffinate product via line 432 containing less solvent than the raffinate in line 160. The recovered water/solvent in line 434 can contain aromatics/non-aromatics separated in and/or entrained from the raffinate wash column 430 from the raffinate introduced via line 160. The recovered water/solvent in line 434 can be introduced to the water stripper 420 to provide a water-lean, hydrocarbon-rich stream via line 422. The non-aromatic rich raffinate via line 432 can be further processed or sent to storage.

The water-lean, hydrocarbon-rich stream in line 422 can be introduced to the water/hydrocarbon separator 470 to provide a recycle hydrocarbon via line 472 and a recovered water stream via line 474. In one or more embodiments, the recycle hydrocarbons via line 472 can be introduced at one or more locations to the extractor 100 for additional processing and/or mixed with the feed line 145 (not shown for convenience of view).

Within the recovery column 440, the bottoms from the stripper 410 is contacted with steam to recover the aromatics. The aromatic compounds are removed from the top of the recovery column 440 and the bottom stream (lean solvent)

462 is recycled back to the extractor 100, although a portion may be sent to solvent regenerator 442 and introduced to recovery column 440 via line 443. The overhead from the recovery column 440 is introduced to the water/hydrocarbon separator 465 to separate the water via line 467 from the product aromatics via line 466. At least a portion of the recovered aromatics can be recycled to the recovery column 440 as reflux.

The process described above, as a whole, is known in the art and further detail here is not necessary to inform the art. See also U.S. Pat. Nos. 7,326,823; 2,773,918; and 3,361,664.

Nevertheless the operation of an aromatic solvent extraction system to form an aromatic extract is exceedingly complicated to operate. Part of the reason for this is that, relative to each aromatic product recovered from the process, the lighter and heavier non-aromatics in a given feed respond differently to changes in process parameters such as the flow rates of the feed and solvent. Thus, a single change in one such parameter can cause widely varying results in the process and products thereof U.S. Pat. No. 7,326,823 solves attempts to control the system by analyzing at least two separate groups of non-aromatics, and, according to the patentee, thereby knowing the relative concentrations of both the lighter and heavier non-aromatics, as opposed to the prior art's single total concentration of non-aromatics, and again according to patentee, the proper adjustments to operating parameters of the process can be made to allow, pursuant to the invention, for tighter control of the final aromatic product(s) purity.

In addition, there continues to be the problem of light impurities building up in the extractive distillation tower and recycle system. These undesired effects result in the incapacity of the extractor to efficiently remove and recover the aromatic compounds within the mixed feedstock.

Typical responses to correcting the incapacity of the extractor include one or more of moving the recycle location, adding more stages of sieved trays, reducing operating rates, or cleaning and/or replacing the sieve tray decks.

The present inventors have discovered that proper monitoring and control of the extraction unit systems in the separation of aromatic hydrocarbons from non-aromatic hydrocarbons, including liquid-liquid extraction processes and extractive distillation processes, and the combination thereof, can result, in embodiments, in at least an order of magnitude improvement in reliability and integrity of the solvent systems and processes for the separation of aromatic hydrocarbons and non-aromatic hydrocarbons.

In addition, giving the operators information about how to respond to certain situations has also proven beneficial. In U.S. Pat. No. 7,739,217 there is disclosed a method for monitoring a polyethylene polymerization system including providing an expert system comprising a database containing knowledge of the polymerization system and an inference engine, the latter comprising rules, receiving and evaluating data from the polymerization system, identifying the first rule as true or false, and displaying the message of the second rule if all the one or more preconditions of the second rule are met. The present inventors have also provided an improved expert system and inference engine wherein the improvement comprises application in extractive distillation controls. As used herein further below, the terms "expert systems" and "inference engine" take the same meaning as set forth in U.S. Pat. No. 7,739,217.

SUMMARY OF THE INVENTION

The invention concerns the monitoring and control of the extraction unit systems in processes for the separation of aromatic hydrocarbons from non-aromatic hydrocarbons in liquid-liquid ("LL") extraction, extractive distillation ("ED"), and the combination thereof.

In embodiments, the invention concerns at least one of: controls to provide proper solvent/feed ratio adjustment, water circulation improvements, feed forward logic (rate and composition), reflux adjustment, recovery and purity targets, and weather response.

In embodiments, the invention also concerns monitoring and control to multiple unit constraints and performance changes over time. The monitoring embodiments include rule based expert systems, variability analysis and online calculations available to the operator to make decisions. The control embodiments include automatic closed loop control of several key variables. The combination (packaging) of the monitoring and control techniques provide a novel approach and operation of an Extraction Unit (LLE and ED).

It is an object of the invention to maintain extraction unit stability (and therefore reliability) by improved control of key unit operating parameters. The monitoring and controls improve unit reliability, capacity and energy utilization throughout the process operating window.

These and other objects, features, and advantages of the present invention will become apparent in the following detailed description, drawings, specific embodiments, experiments, and appendaged claims.

DETAILED DESCRIPTION

Figure 1:
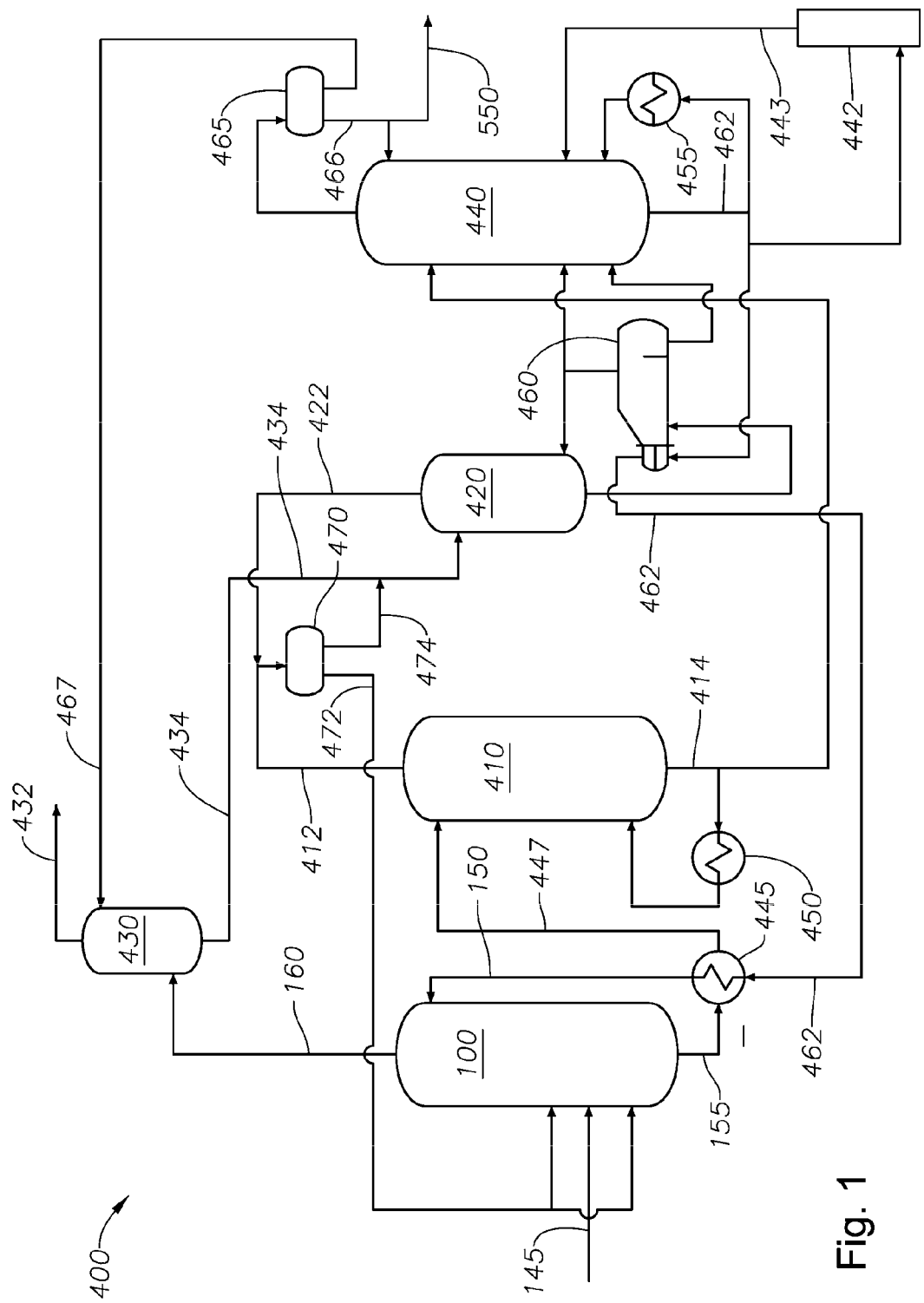
FIG. 1 depicts a simplified schematic view of an illustrative system for separating a hydrocarbon mixture which may be monitored and controlled according to one or more embodiments of the present invention.

The invention concerns an improvement in the monitoring and control systems used in a Liquid-Liquid Extraction Unit (LLE Unit) and an Extractive Distillation Unit (ED Unit) for the separation of aromatic hydrocarbons from non-aromatic hydrocarbons.

As used herein liquid-liquid extraction means a liquid phase process that uses a third component or solvent to effect a chemical separation. As used herein extractive distillation means a vapor-liquid process that uses a third component, or solvent, to effect a chemical separation. An LLE Unit has both a liquid-liquid extraction tower and an extractive distillation tower. An ED unit combines the function of a liquid-liquid extraction tower and extractive distillation tower in a single tower. The present invention is applicable to both types of units and more particularly to such units as are used to extract aromatic compounds, and thus they may be collectively referred to herein as aromatic extraction units or more broadly as extraction units.

Aromatics extraction units remove non-aromatics (NA) from the feed streams and produce an extract stream that contains mostly aromatics (which can include one or more of benzene, toluene, xylenes, and aromatic hydrocarbons having nine carbons ("A9's")) for further processing. There are also some non-aromatics impurities in the extraction unit product that need to be controlled in order to make "on-spec" benzene, toluene, xylene and other aromatic products. The process includes a liquid-liquid extraction tower (or liquid-liquid extractor), an extractive distillation tower (or stripper), or a combination of the liquid-liquid extractor and the stripper in a single tower, and a recovery tower. The disclosure below generally omits discussion of miscellaneous equipment for the steam and water balances and maintaining the "chemistry" of the solvent and water streams, which would be apparent to one of skill in the art.

In embodiments, controls and applications are used to improve the performance of the extraction units downstream of the extraction towers. Advanced multivariable control, such as a dynamic matrix control (DMC) is also used to optimize multiple constraints of many conventional controls and applications.

Monitoring of the extraction process includes, but is not restricted to, three techniques. These include rule based expert systems, abnormal event detections, and online process calculations. The first two of these techniques will be explained immediately below and key process calculation variables will be included in the control description later.

Rule based expert systems can include one or more "rules" that if true could give the operator more information than a simple alarm system. These rules can analyze current conditions or past data. For example, if a new lab result is lower than a pre-selected value after several lab results were above that same value, then the operator can be given advice to make a change to the extraction process. If the second lab sample is again lower than that same (or a different) value, then the operator can be given advice to make a different change.

Rules can be set up to be time-based, such as to give advice only after the rule has been true for a period of time. For example, if a flow is above a pre-selected value, no advice is given until the flow stays above the pre-selected value for 2 hours.

Advice can be given to an operator if a combination of rules are true. For example, if variable A is less than xa and variable B is less than xb then no advice is given; if A is greater than xa and B is less than xb then no advice is given; if A is less than xa and B is greater than xb, then no advice is given; however, if A is greater than xa and B is greater than xb, then advice is given to the operator. Note that the combinations can also include 2 or more rules with standards and/or logic and include time based rules to give the operator advice. It should be noted that the "advice" given to an operator may more broadly be simply "information".

Rules can be set up to suppress other rules. For example if rule A is true by itself, then advice can be given about A. However if B and A are both true, advice can be given about B and the A advice can be suppressed. An example of Rule-based expert systems as applied to a polymerization system is described in U.S. Pat. No. 7,739,217.

In the extraction process, an example of the rule based system would be that if the feed analyzer or a material balance calculation (using flow meters) showed that the feed aromaticity was too high, the operator could be given advice to make a change that would eliminate or more rapidly recover from a plant upset.

Abnormal event detection can be further described in 4 parts. If an abnormal event occurs, then the operator is made aware of the situation such as through rules as described above.

The first type of detection involves analysis of a flow versus a valve position. Data can be collected over time to determine the normal relationship between a valve position and a flow. Note this can be done with the actual flow and the distributed control system ("DCS") output signal to a valve. If the current flow and valve position are outside of the normal relationship, the operator can be made aware of the situation.

The second type of detection involves the normal variability of a proportional-integral-derivative ("PID") controller. Data can be captured over a period of time to determine the normal controllability of the PID controller. There are several aspects that are evaluated. If the controller performance is outside the normal performance, the operator can be made aware of the situation.

The third type of detection is evaluation of the variability of a process variable. Data can be collected over time to determine the normal variability of the variable. If the variability is outside of the normal amount, the operator can be made aware of the situation.

The fourth type of detection uses an online statistical analysis for several variables in the process. Data can be collected over a period of time to determine the normal relationship of the variables. If a variable (or more than one variable) is outside the normal relationship, then the operator can be made aware of the situation.

In the extraction process, several of the above-mentioned techniques could be used to warn the operator of a process problem. An example of a problem would be a valve failure (fail closed) of a water boot draw off from the stripper overhead accumulator. A valve flow detector would warn the operator that there was no flow and valve output would be outside the normal range (in this case the DCS output would probably be full scale open). A PID detector would note that the valve was saturated and the actual flow controller did not match the flow controller/set point and warn the operator. The statistical model would look at the relationship of the flow, valve output, and boot level and warn the operator that there is an abnormal situation in that part of the plant.

There are many places in the extraction process to use some or all of the rules and abnormal event detection techniques. These monitoring techniques have been used to give advice or warn the operator about the process so he/she can take corrective action and eliminate or mitigate an upset which improves reliability.

Figure 2:
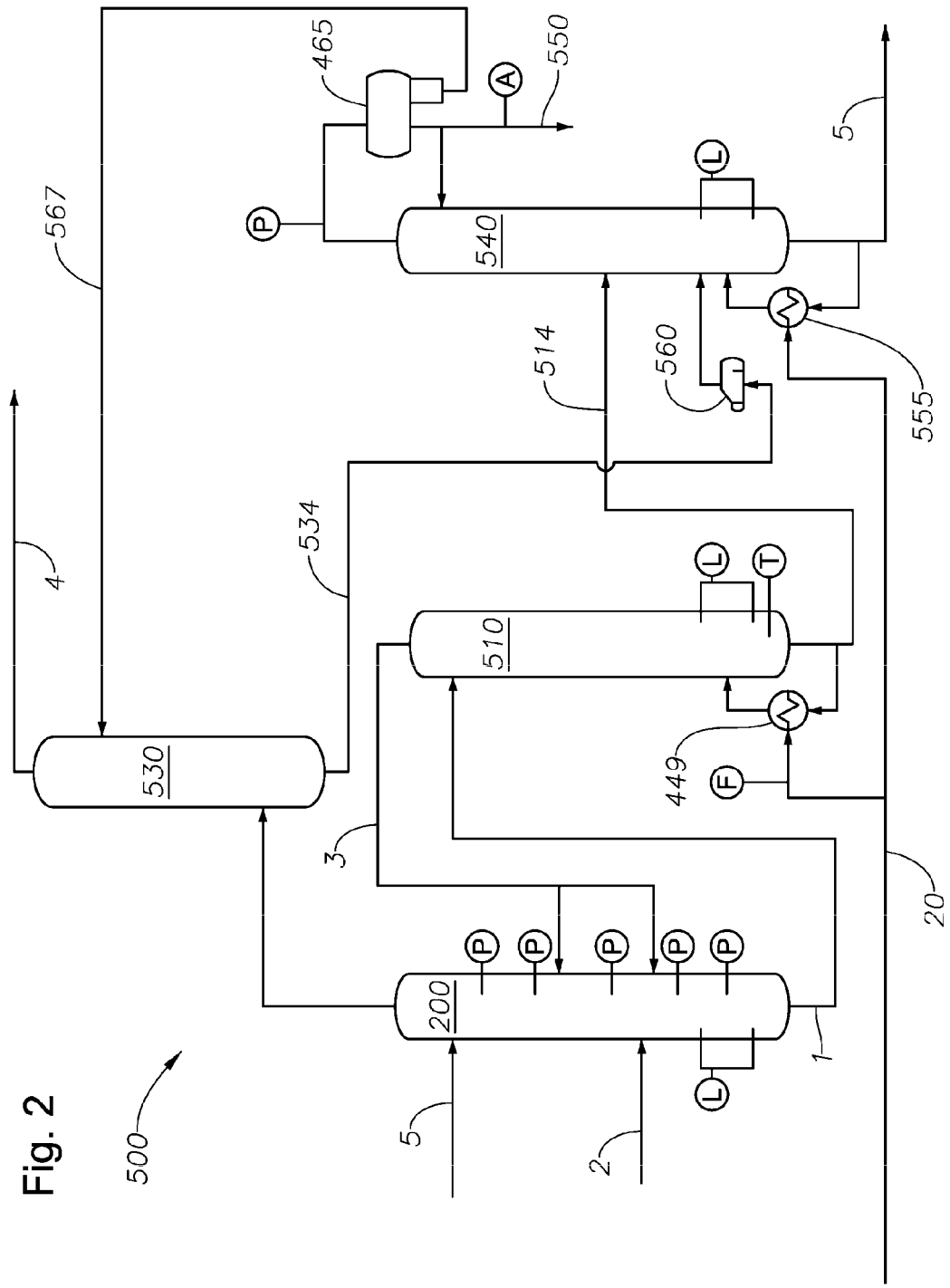
FIG. 2 depicts a simplified schematic view of an illustrative system for separating a hydrocarbon mixture showing monitoring and controls according to an embodiment of the invention.

Basic controls and applications can be used to optimize extraction unit performance. The following is a description of basic applications, which each individually comprise embodiments of the present invention, and which may be combined to provide additional embodiments. Reference will be made to FIG. 2, which is a simplified schematic view of a liquid-liquid extraction unit 500 and controls according to an embodiment of the invention. While one or more heat exchangers are shown in the schematic, unnumbered, by their conventional symbols, other possible heat exchangers and devices such as compressors, valves, column trays and packings, and the like, are not shown for convenience of view but would be apparent to one of ordinary skill in the art. In FIG. 2, the symbol "P" represents a pressure measuring device, "L" is a level measuring device (which detects the interface between the liquid phases when used in extractor tower 200 or the interface between the liquid and gas phases when used in stripper tower 510 and recovery column 540), "F" represents a flow meter or more generally a flow measuring device, "T" represents a temperature measuring device, and "A" represents an analyzer (typically a gas chromatograph or GC) to determine the concentration of one or more species, e.g., non-aromatics. Each of these devices is per se known in the art, and any conventional device useful for measuring "P", "L", "F", "T", and "A" may be used.

As mentioned, FIG. 2 is a simplified schematic and in this case focuses on the hydrocarbon circuit and avoids details of the aqueous and steam phases, e.g., it omits depiction of a water wash tower analogous to apparatus 420 in FIG. 1 to simplify the view. One of skill in the art in possession of the present invention would be able to determine the water wash tower configuration without more than routine engineering.

Extractor Hydrocarbon ("HC") Loading is defined as the amount of hydrocarbon dissolved and entrained in the solvent leaving the bottoms of the extractor tower 200 via line 1. By using a basic application to control this hydrocarbon loading, energy savings and unit stability can be realized.

The basic application is a material balance method used to determine extractor performance and is calculated by the following equation:

$$\% \text{ HC Loading} = (EFF + Rec - Raf) * 100 / (EFF + Rec - Raf + LS).$$

HC Loading means the hydrocarbon material balance of the extractor tower 200 (which may also be referred to herein as extractive distillation tower, liquid-liquid extractor tower, and the like). It is simply defined as the percent of hydrocarbon entering the extractor tower 200, excluding solvent, versus the amount of hydrocarbon exiting via line 1 at the bottom of the extractor tower 200. Other process flows could be used in the calculation, however the present inventors believe that the above flows tend to be more accurate with less variability.

EFF is Extractor Fresh Feed, which means, with reference to FIG. 2, any hydrocarbon feeds to the extractor via fresh feed 2.

"Rec" means Recycle, which with reference to FIG. 2 means the hydrocarbon stream from the stripper tower 510 overhead 3 that is recycled back to the extractor tower 200.

"Raf" is Raffinate, which means, with reference to FIG. 2, aromatics depleted hydrocarbon leaving the process as a byproduct, such as through line 4 from raffinate wash column 530. In embodiments, other flow measuring devices can be used in the process for the raffinate flow based on unit equipment configuration, as could be determined by one of ordinary skill in the art in possession of the present disclosure.

"LS" is the Lean Solvent, which means, with reference to FIG. 2, the solvent 5 loop leaving the bottoms of the recovery column 540 and entering near the top of the extractor tower (connection of conduit 5 between recovery column 540 and extractor tower 200 not shown for convenience of view), typically sulfolane.

In embodiments, the HC loading should be 20-25% on a weight basis, and in other embodiments, the HC loading should be 30-35% on a volume basis, but the ranges may be changed based on, hydrocarbon composition, turnaround intervals and tower internal designs. Unit fouling, over time, impacts phase separation at the bottom of the extractor tower which may result in controlling at a lower HC loading value. Stacking of solvent in the extractor can have the same impact.

In embodiments, HC loading is dependent on lean solvent rate 5 and the feed 2 aromaticity. If the HC loading in stream 1 gets too high, then the extractor tower 200 may extract excessive NAs in the feed into the stripper 510, increasing the recycle 3 back to the extractor. This could result in increased energy usage and decreased overall unit capacity. If the HC loading gets too low, then the extractor 200 may entrain excessive feed into the stripper 510 increasing the recycle 3 back to the extractor 200 and/or use excess solvent circulation in the extraction unit 200 and increase energy requirements.

HC loading ratio (% HC loading) should be used to reset the lean solvent to feed ratio set point (LS/F). If the HC loading ratio is too high, then the LS/F ratio should be increased. If the linear multivariable predictive control (e.g., DMC) is implemented, then the HC ratio should act as a constraint to increase the LS/F if the HC loading ratio gets too high. There should also be advice given to the operator, such as by an alarm, if the HC ratio is not within predetermined ranges.

Extractor Bottoms Interface Level "L" in extractor 200, is used to minimize entrainment of feed in the bottoms of the extractor 200. By controlling this level, settling performance, which translates to capacity, reliability, and energy utilization, is improved.

The liquid interface at the bottom of the extractor 200 is between the feed (aromatics rich) layer and the rich solvent layer. According to aspects of the present invention, there are two different modes for operating extractor 200: "Sealed Deck" and "Rain Deck". In Sealed Deck mode, the rich solvent level, below the feed, is very high in the bottom section of the extractor. The solvent effectively seals the trays (not shown) below the feed tray as a rich solvent layer. In Rain Deck mode, there is less solvent inventory in the bottom area of the extractor and the solvent rains down through the feed layer through the entire trayed section below the feed in the form of little "rain drops". In Rain Deck mode, the interface level is in the bottom section, not unlike the bottoms level of a standard distillation tower. By way of example, the difference in interface level between Sealed Deck and Rain Deck is the difference between the upper portion of "L" and the lower portion of "L" in extractor 200. In either case, if the level gets too low or emulsified due to fouling, then the extractor will entrain feed, including NAs, to the stripper and cause foaming and/or unacceptable stripper tower flooding. Sealed Deck operation is recommended because it allows for more disengaging time between the liquid layers and better solvent inventory control between the extractor, stripper and recovery column.

In the Sulfolane™ Process, the liquid-liquid extraction unit is a closed system with respect to solvent. If the inventory in the stripper and recovery towers, 510 and 540, respectively, are controlled to be constant, then the level "L" and/or amount of solvent in the extractor 200 is maintained by material balance. (Note this excludes the solvent on the trays of the stripper and recovery columns which can change with feed rate and heat duty). In Sealed Deck mode, the interface level is usually well above the top tap (>100%) of the level instrument (usually controlled via a change in a specified lower section of the Extractor tower pressure or "dP"). Improved control can be achieved if the top tap of the interface level is raised to a higher point in the extractor.

Tight control of the stripper 510 (an extractive distillation tower) bottoms level "L" is usually achieved by a fast level to flow cascade for the stripper level and the bottoms flow to the recovery column 540. When in Sealed Deck mode, level control of the recovery column 540 is usually set by the rich solvent flow through conduit 1 from the extractor 200 to the stripper 510. Several feed forwards can help maintain tighter level control. Feed forward controls are detailed in PCT/US2010/033088. For Sealed Deck mode, the extractor level "L" in 200 is usually high and does not enter into the control scheme except as a low override. This control may not be directly applicable if the extractor pressure control scheme impacts the extractor inventory.

If the extractor level "L" in 200 decreases, then raising the lean solvent to feed ratio can sometimes help. Though this is counter intuitive, experience shows that there is some impact depending on the cause of the stacking event. Stacking refers to solvent stacking up on the tower trays and not being able to flow down the tower. Ultimately, cutting feed will always help. For units that "stack" solvent above the feed, the feed is ultimately used to control the interface level. Thus monitoring and controlling (the low side only for a Sealed Deck operation) is required for unit stability. As mentioned, this is also sometimes done with a linear multivariable predictive controller (e.g. DMC) and level as a CV (Control Variable).

The range of the extractor bottoms interface limit should be set to cover the entire range of the level even in sealed deck mode. If the range is too small for sealed deck, and the level starts decreasing from above the top level tap, it may be difficult to catch the level. It is recommended that the bottoms level instrument spans 20% or more of the height of the tower.

The solvents used in the present invention, such as Sulfolane™, have a higher density than the normal hydrocarbon feed to the Extractor tower 200. Because the LLE Extractor is liquid full and the linear flow rates in the tower are low there is essentially little to no flow induced pressure drop (dP). Measuring the dPs for multiple sections of the Extractor can give an estimation of the tower compositions. Though the absolute values of the dPs are important, the trend of the dPs is more important. If a dP across a certain section of the Extractor tower 200 increases (e.g., from one "P" detector to the next), this indicates that more solvent and less feed material is being held in that section of the tower.

This can be very helpful in locating the solvent in various parts of the Extractor tower 200. If dP in an upper section of the tower 200 increases and dP in a lower section of the tower dP decreases, then the solvent is "stacking" in the tower. If this continues, without intervention, then the bottom level as measure by "L" of the Extractor 200 could decrease and lead to an upset (entrainment of free hydrocarbon to the Stripper tower 510) of the unit. Monitoring all of the dPs can give the operator information for unit changes. The information can also be used in a closed loop control system or an advisory system.

Special considerations for rain deck operation: if the extractor bottoms interface level "L" in 210 is in Rain Deck mode, then an operator may choose to control the extractor interface level by manipulating the rich solvent flow. Though Rain Deck is not the preferred extractor mode, as mentioned above, this control scheme is acceptable if the extractor bottoms operation is in rain deck mode. In this case, the recovery tower level "L" in 540 is not controlled and operates independently. If the recovery tower level gets too low and the extractor interface level "L" in 200 and stripper bottoms level "L" in 510 are at there lower limits, then additional solvent is required from outside of the extraction unit. Though the level changes should be slow, if there is a major upset, the recovery tower bottoms level should be maintained to protect the lean solvent pumps.

Special considerations for a "liquid full" (e.g. no $N_2$ bubble) extractor: if the extractor 200 is liquid full (there is no $N_2$ bubble at the top of the extractor) then there is no cushion to material balance changes on the tower so pressure control is achieved by manipulating either the raffinate flow 4 or the rich solvent flow 1. Though not preferred, the rich solvent flow 1 can be used to control the extractor tower 200 pressure but care must be taken to not upset the stripper 510 due to extractor pressure control changes.

With regard to Non-Aromatics (NA) in extract product, Closed Loop Control uses a Non-Aromatics (NA) analyzer "A" in the extractor product rundown line 550 to control the stripper tower 510 reboiler duty 449 supplied with heat by conduit 20, e.g., steam, which also provides heat to the recovery tower 555 reboiler duty. By setting up the control loop in such a matter, energy utilization for making on-spec product is improved.

The NA analyzer "A" in the extract product line 550 is typically a GC (Gas Chromatograph) that can include a total NA analysis or separate different boiling ranges (recommended) of the NAs (typically a Polar (Wax) column). This analyzer should be used in a control scheme to ultimately set the heat duty of the stripper 510. Note that if there are several reboilers, there should be a single calculated value that accurately sums up the heat duties. Increasing the stripper heat duty decreases the NAs in the benzene and toluene products. Changes in stripper tower 510 heat have a different relative effect on the different NA boiling ranges depending on the feed composition and internal tower loading. Using total NAs can lead to heat being added that does not impact heavier NAs in the extract (xylene and heavier boiling range).

The conventional control scheme for the NAs should output to a heat to feed ratio. If the NAs are a controlled variable (CV) with a linear multivariable predictive control (e.g., DMC) the manipulated variable (MV) could be total duty as long as there is feed forward (FF) functionality that changes the heat duty when the feed changes.

It is recommended to use a Stripper heat to extractor fresh feed (EFF) ratio rather than a Stripper heat to Stripper feed ratio to minimize Stripper tower swings and/or upsets. Benzene or toluene tower product streams NAs can also be used in the control stream with sufficient handling of the time lags.

The analyzer control for non-aromatics in the carbon range of C6 and C7 preferably can use two groups of non-aromatics peaks (one for each of C6 and C7 non-aromatic species) to optimize the stripper tower 510 duty instead of a total non-aromatics peak. Usually only one of the NA products specs, e.g., benzene or toluene or xylene, but not more than one, are used at "A" in line 550 using a given system 500. This method of control allows a site to optimize the energy requirement based on the most limiting of the product specs. Note that the separation of the desired aromatics usually occurs with fractionation downstream of the 500 system described herein.

As mentioned in the Background Section, the control scheme outlined in U.S. Pat. No. 7,326,823 has a non-aromatics (NAs) analyzer to control both benzene and toluene non-aromatics (NAs), whereas in a preferred embodiment of this invention, only one product non-aromatic, e.g., benzene, toluene (preferably the latter), or the total extract non-aromatic is analyzed, more preferably with delayed feedback (open or closed loop) from the benzene or toluene product tower analyzers (downstream and not shown in FIG. 2) to control duty.

Except as otherwise set forth above, the stripper tower 510 operates on conventional controls, e.g., overhead pressure via a nitrogen gas ($N_2$) "push/pull" vent system. Control overrides can also be included for non-routine tower operation (e.g., feed composition swings impacting the stripper tower, non-ideal fractionation curves, and the like).

Stripper 510 temperature control alone (without an NA analyzer) is not recommended. If the stripper 510 feed rate via conduit 1, fresh feed composition, total solvent, water content, or other measureable parameter change, then the temperature will not properly infer NAs in the extract. This is also true for temperatures adjusted for stripper tower pressure. During an upset, relying on a temperature control can drive the unit the wrong way.

However, temperature taken at "T" (or a pressure adjusted temperature taken at "T") in 510 is a good inference of NA concentration if nothing else changes on the stripper 510. Due to analyzer time lag (as a result of, among other issues, process and analyzer capability), the temperature can be a useful indicator. Because temperature taken at "T" in 510 is a faster indicator than a GC analyzer typically used at "A" in line 550, during a sudden rainstorm, the temperature will react more quickly than the analyzer. This temperature "T" can be any-where in the stripper tower 510 as long as it infers NA composition in the extract product. Multiple indicators "T" can be used.

To take advantage of the good aspects for both of these variables, a temperature controller "T" with a set point (SP) that is lower than the average temperature in 510 over a period of time can handle the rainstorms but normal control should be from the analyzer "A" in line 550. In conventional controls, a temperature controller with the right SP and the NA analyzer controller can output to a high signal select which ultimately sets the stripper duty. In other words, the analyzer is usually in control (selected) unless the temperature dips down quickly below the average temperature recently measured, details of which may be determined by one of skill in the art in possession of the present invention. For linear multivariable predictive control (e.g., DMC), both the stripper temperature and the NAs should be CVs with the MV the heat duty.

The temperature SP for conventional controller and/or the lower control limit for linear multivariable predictive control (e.g., DMC) temperature CV must be chosen so that the NA controller is normally selected and the temperature is only selected during a sudden weather change. A calculation should be built to determine the rolling average temperature over the last 4 to 6 hours. A bias of 1.5 to 2.0° F. should be subtracted from that average and then be used for the SP or DMC lower control limit of the temperature CV.

When the extractor 200 entrains hydrocarbon to the stripper 510, the stripper 510 gets overloaded and separation fails as it is not designed to handle the NA phase at the top of the tower. The entrainment can happen gradually or rapidly. There are two instrument readings, as described below, that detect increased variability during a gradual move to entrainment. Properly alerted by rules as described above or by simple alarms, the operator can adjust the extractor 200 to mitigate a serious upset.

The two instrument readings used for monitoring are the stripper dP measured by one or more pressure sensor "P" (not shown) in 510, particularly in the upper portions of stripper 510, and the overhead flow measured by a flow measuring device "F" (not shown). The process values (PVs) of both of these instruments normally fluctuate but during entrainment fluctuate more rapidly with increasing amplitude. Calculating the variability of the instruments over short periods of time and informing the operator of the variability at levels above the typical noise can allow the operator to make a change on the extractor. Determination of which calculation to pick depends on the instrument installation at the site. Weather events can give false positives if the filters of the calculations and alarm points are too close to the typical noise. One of ordinary skill in the art, in possession of the present disclosure, can make such determinations.

Preferably the calculations should use the linear difference between adjacent values (not a square function). This way one atypical value will not skew the relative noise calculation. There are several calculations that could be used.

For Stripper Tower Duty Feed Forward, this control application sits below (i.e., is secondary in control hierarchy to) the advanced control strategies listed previously. The control monitors feed rate in line 2 (such as by flow meter "F" not shown) to the extraction unit 200 and calculates duty changes needed to maintain reliable unit 500 operations.

For Recovery Tower Bottoms Level control ("L" in 540), the bottoms level of the recovery column 540 is preferably used to reset the rich solvent flow 1, particularly for Sealed Deck operation. This controller should not be tuned as tightly as the stripper level control because rapid changes in the rich flow with no input changes to the extractor can impact the mass transfer equilibrium and lead to potential entrainment to the stripper.

Because the lean solvent to feed ratio is used to control the bottoms flow from the recovery column, the only other choice for bottoms level control for this column is the flow into the column. This flow is needed for the stripper bottoms level control which is another reason the stripper bottoms is controlled tightly. Thus backing up to the rich solvent from the Extractor is the only available knob to control the Recovery Column bottoms level. Using proper tuning and proper feed forward applications works well. This level can slowly drift a little so tuning can be relaxed so as not to disturb the stripper tower.

Special consideration (R) for rain deck operation are addressed below.

If the extractor interface level is controlled, then the recovery tower bottoms level can not be controlled since the sulfolane unit is a closed system for the solvent. The recovery tower bottoms level floats and should be monitored to determine when to add solvent to the unit. Again, during a major upset, the recovery tower bottoms level should be maintained to protect the lean solvent pumps.

The UOP Sulfolane™ Process is a liquid-liquid extraction process to recover high-purity aromatics from hydrocarbon mixtures, such as reformate, pygas, or coke-oven light oil. This process is described in the Handbook of Petroleum Refining Process, 2nd edition (1996) p. 2.13, incorporated herein by reference as to that description.

All embodiments of the above detailed control system can apply to liquid-liquid extraction units. They also apply to an extractive distillation unit and can be adapted thereto by one of ordinary skill in the art in possession of the present disclosure.

The extracting solvent is any liquid that preferentially extracts aromatic hydrocarbons over aliphatic hydrocarbons. The boiling point of the extraction solvent should be higher than the boiling point of the aromatic hydrocarbons being extracted (i.e., it should have a boiling point of at least 100° C. and preferably between about 200° C. and about 300° C.) so that it is not evaporated during stripping. In embodiments, the preferred extracting solvent is Sulfolane™, which is commercially available from numerous sources. In other embodiments the solvent is selected from glycols, such as di-, tri-, and tetraethylene glycol, and nitrogen-containing species such as N-methyl pyrrolidine. Mixtures of such solvents can be used.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art. Various terms have been defined above. To the extent a term used herein is not specifically defined, reference should be made first to the prior art set forth herein, provided it is consistent with the use of the term herein, and then to the Handbook of Petroleum Refining Process, 2nd edition (1996). Furthermore, all patents, test procedures, and other documents cited in this application are fully incorporated by reference to the extent such disclosure is not inconsistent with this application and for all jurisdictions in which such incorporation is permitted. Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. In a process for separating aromatics from a hydrocarbon mixture feed comprising aromatics and non-aromatics by use of a solvent which preferentially absorbs aromatics, in a system comprising a liquid-liquid extraction (LLE) unit or an extractive distillation (ED) unit, wherein said solvent is mixed with said hydrocarbon mixture and said solvent preferentially absorbs said aromatics to provide a first aromatics-depleted hydrocarbon stream, relative to said hydrocarbon mixture feed, and a first aromatics-enriched solvent stream, relative to said hydrocarbon mixture, and wherein both said first aromatics-depleted hydrocarbon stream and said first aromatics-enriched solvent stream are further processed in said LLE unit or ED unit to produce a final aromatics-depleted stream and a product comprising at least one of the aromatics selected from the group consisting of benzene, toluene, and xylene, the improvement comprising:

(a) monitoring the amount of hydrocarbon feed entering an extractor tower of said LLE unit or ED unit, the amount of hydrocarbon recycled to said extractor tower from a stripper tower of said LLE unit or ED unit, the amount of hydrocarbon removed from said LLE unit or ED unit, and the amount of lean solvent entering said extractor tower, wherein said amounts are monitored by flow measuring devices and conveyed to a controller;

(b) calculating the hydrocarbon loading of the LLE unit or ED unit in said controller by the following equation:

$$\% \text{ HC Loading} = (EFF + Rec - Raf) * 100 / (EFF + Rec - Raf + LS)$$

wherein "EFF" is the amount of hydrocarbon feed entering said extractor tower, "Rec" is the amount of hydrocarbon recycled to said extractor tower from said stripper tower, "Raf" is the amount of hydrocarbon removed from said LLE unit or ED unit, and "LS" is the amount of lean solvent entering said extractor tower; and (c) sending a signal from said controller to flow metering devices to control the amount of lean solvent and/or feed based on whether the HC loading is above or below a predetermined set value to adjust the lean solvent to feed ratio in said extractor tower to manage the amount of non-aromatics in the aromatics product, the amount of aromatics in the aromatics depleted hydrocarbon stream, flow rates, and energy usage and to improve reliability for the LLE unit or ED unit.

2. The process of claim 1, wherein said extractive distillation unit is a liquid-liquid extraction distillation unit.

3. The process of claim 1, wherein when said HC loading is greater than 25 wt % or 35 vol %, said controller sends a signal to the flow metering devices to either increase the amount of lean solvent or decrease the amount of feed introduced to said extractor tower.

4. The process of claim 1, wherein when said HC loading is less than 20 wt % or 30 vol %, said controller sends a signal to the flow metering devices to either decrease the amount of lean solvent or increase the amount of feed introduced to said extractor tower.

* * * * *